(12) United States Patent
Manian

(10) Patent No.: US 9,523,640 B2
(45) Date of Patent: Dec. 20, 2016

(54) METHOD OF FLUORESCENT MEASUREMENT OF SAMPLES, AND DEVICES THEREFROM

(75) Inventor: Bala S. Manian, Los Altos Hills, CA (US)

(73) Assignee: Reametrix, Inc., San Carlos, CA (US)

( * ) Notice: Subject to any disclaimer, the term of this patent is extended or adjusted under 35 U.S.C. 154(b) by 208 days.

(21) Appl. No.: 13/034,302

(22) Filed: Feb. 24, 2011

(65) Prior Publication Data

US 2012/0104280 A1    May 3, 2012

(30) Foreign Application Priority Data

Nov. 3, 2010    (WO) .. INTELL PCT/IB2010/054965

(51) Int. Cl.
*G01N 21/64* (2006.01)
*G02B 21/00* (2006.01)

(52) U.S. Cl.
CPC ...... *G01N 21/6428* (2013.01); *G01N 21/6452* (2013.01); *G02B 21/0076* (2013.01)

(58) Field of Classification Search
CPC ............ G01N 21/6428; G01N 21/6452; G02B 21/0076
USPC ........................................... 250/458.1, 459.1
See application file for complete search history.

(56) References Cited

U.S. PATENT DOCUMENTS

| | | |
|---|---|---|
| 4,144,452 A | 3/1979 | Harte |
| 4,284,412 A | 8/1981 | Hansen et al. |
| 4,461,973 A | 7/1984 | Kaufman et al. |
| 5,053,197 A | 10/1991 | Bowen |
| 5,104,813 A | 4/1992 | Besemer et al. |
| 5,132,242 A | 7/1992 | Cheung |
| 5,147,609 A | 9/1992 | Grenner |
| 5,194,300 A | 3/1993 | Cheung |
| 5,252,834 A * | 10/1993 | Lin ............................ 250/458.1 |
| 5,381,224 A | 1/1995 | Dixon et al. |

(Continued)

FOREIGN PATENT DOCUMENTS

| | | |
|---|---|---|
| DE | 4307042 A1 | 9/1994 |
| EP | 0515129 A2 | 11/1992 |

(Continued)

*Primary Examiner* — David Porta
*Assistant Examiner* — Gisselle Gutierrez
(74) *Attorney, Agent, or Firm* — Thomas Schneck

(57) ABSTRACT

The invention provides a method and device for fluorescent measurement of a volume of liquid sample in a sample carrier. The method includes impinging an incident beam having an excitation wavelength and a focus diameter on the sample in a two dimensional scan, such as an R-theta scan or a spiral scan, with a laser spot that identifies a volume of interest where higher levels of fluorescence exist. The laser spot is displaced relative to the sample volume in three dimensional space. The laser spot is translated in the depth direction of the volume of interest to detect one or more emitted fluorescence signals. A depth profile and a thickness of the sample carrier obtained from the one or more emitted fluorescence signals, are used for measuring normalized bulk fluorescence. Further, at least one microvolume of interest is obtained from the depth profile, and the incident beam is focused on the microvolume of interest to obtain at least one concentrated emitted fluorescence signal that is representative of the bulk concentration of fluorescence of a fluorophore.

37 Claims, 11 Drawing Sheets

(56) References Cited

U.S. PATENT DOCUMENTS

| | | | |
|---|---|---|---|
| 5,479,024 A | 12/1995 | Hillner et al. | |
| 5,532,873 A | 7/1996 | Dixon | |
| 5,547,849 A * | 8/1996 | Baer et al. | 435/7.24 |
| 5,747,349 A | 5/1998 | van den Engh et al. | |
| 5,784,152 A | 7/1998 | Heffelfinger et al. | |
| 5,786,219 A | 7/1998 | Zhang et al. | |
| 5,866,433 A | 2/1999 | Schalkhammer et al. | |
| 5,939,326 A | 8/1999 | Chupp et al. | |
| 6,020,591 A * | 2/2000 | Harter et al. | 250/458.1 |
| 6,159,686 A * | 12/2000 | Kardos et al. | 435/6.14 |
| 6,228,652 B1 | 5/2001 | Rodriguez et al. | |
| 6,514,770 B1 | 2/2003 | Sorin | |
| 6,653,152 B2 | 11/2003 | Challener | |
| 6,700,951 B2 | 3/2004 | Sumii | |
| 6,737,238 B2 | 5/2004 | Suzuki et al. | |
| 6,838,289 B2 | 1/2005 | Bell et al. | |
| 6,905,881 B2 | 6/2005 | Sammak et al. | |
| 6,905,885 B2 | 6/2005 | Colston et al. | |
| 6,979,830 B2 | 12/2005 | Dietz et al. | |
| 7,024,061 B2 | 4/2006 | Liedenbaum et al. | |
| 7,034,317 B2 | 4/2006 | Olszak et al. | |
| 7,043,287 B1 * | 5/2006 | Khalil et al. | 600/310 |
| 7,102,737 B2 | 9/2006 | Eyolfson et al. | |
| 7,295,316 B2 | 11/2007 | Boege et al. | |
| 7,300,800 B2 | 11/2007 | Bell et al. | |
| 7,528,384 B2 | 5/2009 | Gratton et al. | |
| 8,072,585 B2 | 12/2011 | Wang et al. | |
| 8,507,886 B2 | 8/2013 | Gotz et al. | |
| 2003/0133840 A1 | 7/2003 | Coombs et al. | |
| 2003/0151735 A1 | 8/2003 | Blumenfeld et al. | |
| 2003/0156323 A1 | 8/2003 | Overbeck | |
| 2004/0002085 A1 | 1/2004 | Schembri et al. | |
| 2004/0239951 A1 | 12/2004 | Yamanishi et al. | |
| 2005/0122579 A1 | 6/2005 | Sasaki | |
| 2006/0003320 A1 * | 1/2006 | Miller et al. | 435/5 |
| 2006/0073611 A1 | 4/2006 | Grainger | |
| 2006/0256338 A1 | 11/2006 | Gratton et al. | |
| 2007/0207513 A1 | 9/2007 | Sorensen et al. | |
| 2011/0031420 A1 | 2/2011 | Gotz et al. | |
| 2012/0107950 A1 | 5/2012 | Manian | |
| 2014/0170760 A1 | 6/2014 | Tanabe et al. | |

FOREIGN PATENT DOCUMENTS

| | | |
|---|---|---|
| EP | 0681178 A1 | 11/1995 |
| EP | 1219950 A1 | 7/2002 |
| EP | 1219951 A1 | 7/2007 |
| FR | 2924805 A1 | 6/2009 |
| GB | 2443715 A | 5/2008 |
| JP | 7229828 A | 8/1995 |
| JP | 7280741 A | 10/1995 |
| JP | 2000081387 A | 3/2000 |
| JP | 2001242082 A | 9/2001 |
| JP | 2002323437 A | 11/2002 |
| JP | 2007020557 A | 2/2007 |
| NL | 9000622 A | 10/1991 |
| WO | WO 84/00817 A1 | 3/1984 |
| WO | WO 95/08118 A1 | 3/1995 |
| WO | WO 97/02482 A1 | 1/1997 |
| WO | WO 98/35223 A1 | 8/1998 |
| WO | WO 99/09455 A1 | 2/1999 |
| WO | WO 99/54736 A1 | 10/1999 |
| WO | WO 00/50872 A2 | 8/2000 |
| WO | WO 0071991 | 11/2000 |
| WO | WO 2006/118420 A1 | 5/2006 |

* cited by examiner

METHOD OF FLUORESCENT MEASUREMENT OF SAMPLES, AND DEVICES THEREFROM

CROSS REFERENCE TO RELATED APPLICATION

This application claims priority from International Application No. PCT/IB2010/054965, filed on Nov. 3, 2010.

FIELD OF THE INVENTION

The invention relates generally to fluorescent measurement method and device and more specifically a method to perform simultaneous measurement of bulk fluorescence and event fluorescence data and devices therefrom.

BACKGROUND OF THE INVENTION

Fluorescent measurements are useful for a variety of applications. One big area of application for such measurements is in diagnostics. However, in the making and using devices that are based on fluorescent measurements, several problems are encountered.

The use of fluorescent measurements in different applications is known in the art. For example, in patent WO 0050872(A2) and WO 9909455(A1), an apparatus capable of measuring quantities of biological or other types of samples that have been labeled using any of a variety of techniques including fluorescence, radioisotopes, enzyme activated light emitting chemicals and enzyme activated fluorescent materials is provided. The provided scanner includes a source module that preferably contains an internal laser emitting two different wavelengths of approximately the same intensity. An optional external light source may be coupled to the source module, thus adding further flexibility through the addition of other wavelengths (e.g. UV, visible, mid-IR, and IR). In NL 9000622(A), the illumination system uses a coherent light source, e.g. an argon ion laser and a microscope lens assembly where the detection system which also uses the microscope lens, can detect several fluorescing colourings at various wavelengths, as well as scattered light signals. The optical focussing and tracking system uses a contactless infra-red light technique. A confocal laser scanning microscope is used for forming an image. The invention mentioned in FR2924805 has a converter of linear polarization in radial polarization of the light beams emitted by the light source which is laid out between the light source and the interferometer thus resulting in a high resolution image. Abstract of GB 2443715 (A) describes a portable spectrophotometer suitable for harsh environments is used to identify and quantify a substance in a sample. It comprises a housing containing a light source, a probe for transmitting light from the light source to a sample to be analyzed and a probe for receiving light from the sample to be analyzed. A microprocessor comprises a reference library and an algorithm to identify a compound or class of compounds in the sample. However, the systems, methods and apparatus will allow for only one type of detection: either bulk or event based detection.

In case of identifying and enumerating specified blood cell subclasses, U.S. Pat. No. 4,284,412, states that a blood sample is first incubated with a reagent including antibodies to the lymphocyte subclass to be identified, the antibodies being directly or indirectly made fluorescently responsive to particular light (e.g. argon ion laser). The sample is illuminated, a cell at a time, by such focused coherent light, and forward light scatter, right angle light scatter, and fluorescence are detected and used to identify and enumerate cells of the specified subclass. WO 9508118 (A1) discloses a method and apparatus for a biological sample assay comprising forming a potentially reactive system of the sample and a fluorophore-conjugated reagent specific to a target compound, separating reacted and unreacted reagent and detecting fluorophore fluorescence in one of the separated components, the detected fluorescence being at near infrared wavelength. However, the methods involved herein are quite cumbersome and require multiple steps, and the devices are not conducive for use in harsh environments.

WO 2006118420(A1) and US 2003133840(A1) are directed towards providing convenient and economical alternatives for detection of signals arising out of an analysis device. However, they don't address the problems related to sample preparation and the analysis. Further, the sophisticated devices described in the aforementioned patent publications are not very conducive for rapid calibration and problem-identification and if necessary subsequent servicing.

An apparatus for optical testing of samples is disclosed in EP 0515129. The apparatus includes an apparatus for receiving a plurality of samples to be tested, light detection apparatus, apparatus defining light paths-extending from the plurality of samples to the light detection apparatus and apparatus for exposing the light detection apparatus to light received from individual ones of the plurality of samples along the light paths. JP 7229828 describes an invention to measure in-plane and vertical double refraction of an optical disc substrate accurately, quickly and conveniently by setting the incident plane in a plurality of directions and making an optical beam incident on the optical disc substrate. JP 2000081387(A) also describes a similar method. The invention in JP 7280741(A) detects the degree of the position shift of a true center of a wafer and a rotary center and correct the coordinates values of a foreign substance data in a surface inspecting apparatus so that at the time of observation of the foreign substance by a SEM (scanning electron microscope), a desired foreign substance can be captured easily. Similarly in JP 2001242082 (A), the sample chip containing multiple biological samples is optically scanned by means of the biological sample optical scanning device for identifying a biological sample labeled with the fluorescent material. Fluorescence from the fluorescent material excited by the light radiated from an objective lens is received by means of a light receiving member via the hollow part of a rotor to output an electric signal thus providing a biological sample optical scanning device greatly shortening an optical scanning time on a sample chip for efficient analysis and having excellent fluorescence detection sensitiveness of fluorescent material used for labeling the biological sample. DE 4307042(A1) describes the use of a laser diode which emits light in the red or near infrared wavelength region for excitation. It is possible, in combination with dye molecules whose absorption range overlaps with the laser wavelength, to reduce the background fluorescence, considerably to reduce the constructional cost, and simultaneously to use the evanescent wave when a time-saving one-step test is constructed for the optical detection of molecules, biomolecules and microorganisms.

In EP 0681178 (A1), an apparatus and method of the invention disclose a scanning imaging cytometer wherein an unprocessed biological fluid sample is reacted with a fluorescently-labeled binding agent. A spatial filter of a sufficient pinhole diameter is selected to allow simultaneous volumetric detection of all fluorescent targets in each columnar region. JP 2007020557 (A) provides an apparatus for measuring microorganisms subjected to fluorescent dyeing; wherein at a point during the measurement, if a preset numerical value is exceeded, an alarm can be given or the measurement can be suspended. WO 9835223(A1) describes a method for increasing the accuracy and the types of data measurements of laser scanned dye stained cells, in a single sample, by means of multiple assays, utilizing cell positions as a factor in merging data measurements. Change in lasers, use of different cell dye stains and different treating reagents provide additional data regarding cells of the sample and fixing of cell positions in the first assay permits merging of the data obtained in subsequent assays. Such analysis systems may be used for a single-type of analysis, however, in many practical situations, multiple analyses are required for effective identification and quantification of analytes.

EP 1219950 (A1), EP 1219951(A1) and JP 2002323437 (A) discloses a method wherein the volume of single red blood cells or other particles suspended in liquids are determined by fluorescent labeling the sample. The cell volume is determined using fluorescence intensity values measured (i) in a first area comprising a single cell, (ii) in a second area close to that cell, and (iii) in said second area, after changing the cuvette thickness by a known amount. As already noted, making parts that are well-machined having no surface irregularities are difficult, especially for those parts that are generally used once, such as sample carriers. WO 8400817(A1) mentions a method and apparatus for fluorescent immunoassay which utilizes total internal reflection at the interface between a solid phase and a liquid phase of lower index of refraction to produce an evanescent wave in the liquid phase. In WO 9702482(A1), apheresis samples are incubated with a surfactant which allows the intercalating dye to enter the WBC. A scanning instrument scans, identifies and enumerates the WBC in the apheresis sample. The system uses an adaptive intensity threshold to identify target fluorescent particles. In these cases, however, sample preparation methods and reagents may be expensive, and since liquid samples are being used, it may not be conducive for transportation and handling in a remote, scant-resource, harsh environments.

A microscale binding assay, analyte binding array, and kits are disclosed in WO 9954736(A1) which exploit the mass action law to harvest analyte from a liquid sample. This approach, coupled with direct fluorescence detection in the NIR, yields maximal signal intensity and low background for optimal sensitivity. US 2007207513 (A1) also provides methods, products and kits for identifying an analyte in a sample but the method includes combining the sample with a first reactant capable of specifically coupling to the analyte. The first reactant is then coupled to beads. The method further includes identifying the analyte in the sample by detecting the modified substrate bound to the surface of the beads and/or the reactants bound to the beads. U.S. Pat. Nos. 7,300,800 and 6,838,289 utilized a combination of fluorescent labels for labeling particles and an analyte specific fluorescent analyte detection dye. The particles contain a combination of fluorescent labels for coding the particles and an analyte specific fluorescent dye. Near infrared (NIR) fluorescent labels useful in the detection system are also provided. U.S. Pat. No. 6,905,885 describe a portable pathogen detection system that accomplishes on-site multiplex detection of targets in biological samples. The system includes: microbead specific reagents, incubation/mixing chambers, a disposable microbead capture substrate, and an optical measurement and decoding arrangement. U.S. Pat. No. 6,905,881 provides a microbead-based test plates and test methods for adjusting fluorescence imaging systems involving using a plate with fluorescent microbeads bound to a surface. U.S. Pat. No. 5,747,349 provide a method and apparatus for rapid measurement of a fluid bulk analyte, requiring only microscale volumes. Several fluid bulk analytes can be measured simultaneously and, for biological samples, the cell content can also be measured simultaneously. The invention comprises reporter beads for chemical analysis of fluid bulk properties such as pH, oxygen saturation and ion content. Despite the availability of several elegant solutions, such methods and devices are useful for single type of analysis only.

U.S. Pat. No. 5,866,433 describes an optochemical fluorescence sensor with a biorecognitive layer for measuring the concentration of one or more analytes in a sample is provided with at least one island layer which is applied on a sensor substrate. The invention in U.S. Pat. No. 5,786,219 describes novel fluorescently labeled microspheres, where the microspheres possess at least one internal fluorescent spherical zone. The invention also describes the method of preparing the novel microspheres, the method of calibrating microscopy instrumentation using the novel microspheres, the method of using the novel microspheres as distinct labels for combinatorial analysis and the use of the labeled microspheres as tagging agents and tracers. U.S. Pat. Nos. 5,194,300 and 5,132,242 describe methods of making highly fluorescent latex microsphere having a diameter of less than five hundred angstroms and have more than five thousand fluorescent markers per sphere. The microspheres are prepared by reacting an acrylic latex bead with a diamine and a fluorescent amine at elevated pH. U.S. Pat. No. 5,147,609 describe an assay element suitable for use in an automated analytical test instrument for assaying a fluid sample. The element includes a thin porous member possessing a high degree of capillarity such as a fibrous mesh pad supported within a guide defined by surfaces contiguous the porous member. U.S. Pat. No. 5,104,813 provides a dilution and mixing cartridge that allows single (or multiple) dilutions of a sample with a diluent in a disposable cartridge in which a measurement, such as optical density, is made. Addition of sample to the device automatically measures the sample, and addition of diluent automatically causes a fixed ratio of sample and diluent to enter a receiving chamber, in which mixing and measurement can take place. U.S. Pat. No. 5,053,197 describes a diagnostic assay module for analytical procedures in which an optical signal developed by interaction between a component in a sample fluid, such as an analyte in a biological fluid, and one or more reagents in a resilient assay element is read by optical means. U.S. Pat. No. 4,144,452 describes a fluorometric system to determine the kind and amount of substances derived from a biological fluid (e.g., serum or urine) or tissue in which the substances to be detected (e.g., antigen, antibody, hormone or enzyme) are coated onto a substrate surface in fluorescent form. Multiple coating areas of different samples may be employed. The fluorometric system includes a source of filtered light to excite fluorescence, an optical system for conducting the excitation light to such coating, and optical systems for receiving emitted fluorescence and for detecting the same. The invention in US 2006073611(A1) relates to methods of assaying the levels of proteins or antibodies in a test sample, and in particular, it relates to a method of determining the relative abundance of a plurality of proteins in a test sample compared to a reference. U.S. Pat. No. 7,295,316 illustrates a fluorometry device and method adapted to determine concentration of spectrally distinguishable species in a biological sample with a plurality of movable optical devices. U.S. Pat. No. 7,024,061 portrays an optical scanning device for scanning with a radiation beam a substantially circular track of an information layer. U.S. Pat. No. 6,979,830 describes methods and instrumentation for performing charge coupled device (CCD)-based confocal spectroscopy with a laser spot array are provided. The methods and instruments of the invention are useful in any spectroscopic application, including, but not limited to, microscopy and microvolume laser scanning cytometry (MLSC). In U.S. Pat. No. 6,514,770 immunoassay methods for measuring the concentration of an analyte in a test specimen are described. The methods use an immunoreagent, where one of the analyte and the immunoreagent is an antigen, and the other of the analyte and the immunoreagent is an antibody which specifically binds to the antigen. U.S. Pat. No. 4,461,973 describes a method and apparatus for measuring the concentration of a substance capable of absorbing infrared, visible or ultraviolet radiation energy, the substance being in a mixture. The method and apparatus involve passing a beam of radiant energy having predetermined spectral response characteristics through the mixture, modulating the beam at a predetermined frequency. In U.S. Pat. No. 7,102,737 a method and apparatus for detection of a particular material, such as photo-resist material, on a sample surface are disclosed. A narrow beam of light is projected onto the sample surface and the fluoresced and/or reflected light intensity at a particular wavelength band is measured by a light detector. U.S. Pat. No. 6,228,652 mentions a blood analyzing instrument includes a single transducer for simultaneously measuring the DC volume, RF conductivity, light scattering and fluorescence characteristics of blood cells passing through a cell-interrogation zone. In U.S. Pat. No. 5,939,326 a device for analyzing a whole blood sample is provided. The device comprises a conventional hematology analyzer integrated with a fluorescence cyometry analyzer. U.S. Pat. No. 5,784,152 describes a method and apparatus of analyzing samples contained in a microplate. The instrument is capable of measuring fluorescence, luminescence, and/or absorption within multiple locations within a sample well.

All of the methods and devices mentioned herein suffer from the drawbacks that include at least one of being expensive, using expensive reagents and consumable/disposable parts, not capable of being used in a harsh and resource-scant environment, and are at best capable of very limited analysis, to name a few problems. Hence, there is a dire need to make available a device that can address all these drawbacks, and accordingly a method that can be adaptable to be used in such a device.

SUMMARY OF THE INVENTION

In one aspect, the invention provides a method for measuring fluorescence. The method comprises providing a sample in a sample carrier, wherein the sample contains at least one fluorophore. The method then comprises providing a light source to generate an incident beam having an excitation wavelength and a focus diameter to impinge on the sample to yield a laser spot that defines a sample volume for measuring fluorescence. The method further comprises displacing the laser spot relative to the sample volume in a three dimensional space defined by the sample, wherein the sample volume comprises at least one individual volume of interest.

In another aspect, the invention provides a fluorescence measuring device. The device comprises a sample assembly for receiving a sample carrier that comprises a sample. The device also comprises a light source for generating an incident beam. The device further comprises a means for displacing the laser spot relative to the sample volume.

In yet another aspect, the invention provides a method for analyzing a sample. The method for analyzing comprises preparing a sample for analysis. The method then includes acquiring simultaneous measurement data from the sample, wherein the simultaneous measurement data is representative of one or more fluorescence events for the at least one individual volume of interest and a normalized bulk fluorescence for the sample. The method for analyzing further comprises using the simultaneous measurement data to determine a disease condition.

BRIEF DESCRIPTION OF THE FIGURES

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As used herein and in the claims, the singular forms "a," "an," and "the" include the plural reference unless the context clearly indicates otherwise.

As used herein, sample means any substance that requires analysis for the purposes of either identification of one or more analytes, or measurement of properties, or quantification of one or more analytes, or the like, or combinations thereof. Sample may be in any given physical form, and this includes solution, suspension, emulsion, solid, and the like. In some embodiments, sample is an aqueous solution, and in other embodiments, sample is a suspension in an aqueous medium. Samples are typically derived from any number of sources. In one instance, sample is derived from a body fluid. Body fluids may be derived from human or animal sources, such as primates, dogs, and the like. Body fluids include saliva, sweat, urine, sputum, mucous, semen, and the like. In another instance, sample may be derived from a fluid source, such as water from a reservoir. In yet another instance, sample may be derived from a location such as a cotton swab of a baggage at security checkpoints, which may be used as such or may be suspended in a suitable solvent for analysis.

Samples useful in the invention comprise at least one fluorophore. Fluorophore as used herein means any moiety that is capable of being fluorescent upon excited by a radiation corresponding to the excitation wavelength of the fluorophore, after which it emits radiation having a wavelength, which is referred to as emission wavelength. The fluorophore is attached to the remaining portion of the sample through physical linkages or through chemical linkages. Methods of incorporating fluorophores onto other materials are well-known to one of ordinary skill in the art, and can be arrived at without undue experimentation.

Sample is generally made available for the aforementioned purposes in a suitable sample carrier. The nature of the sample carrier depends on the nature of the sample and analysis being performed. In some instances, sample carrier is a cuvette, in other instances, sample carrier is a well, in yet other instances, sample carrier is a plate. The nature of the sample carrier will also accordingly determine the characteristics of the sample carrier. Thus, a cuvette is characterized by a wall thickness, a depth, a volume, and the like, while a well is characterized by a depth and a volume, and a plate is characterized by width. Sample may be pipetted into the sample carrier, or may be poured in, or may be added as a solid and spread along the surface through application of shear force, or prepared in situ in the sample carrier in a suitable medium, or through any other means known to those of ordinary skill in the art.

Figure 1:
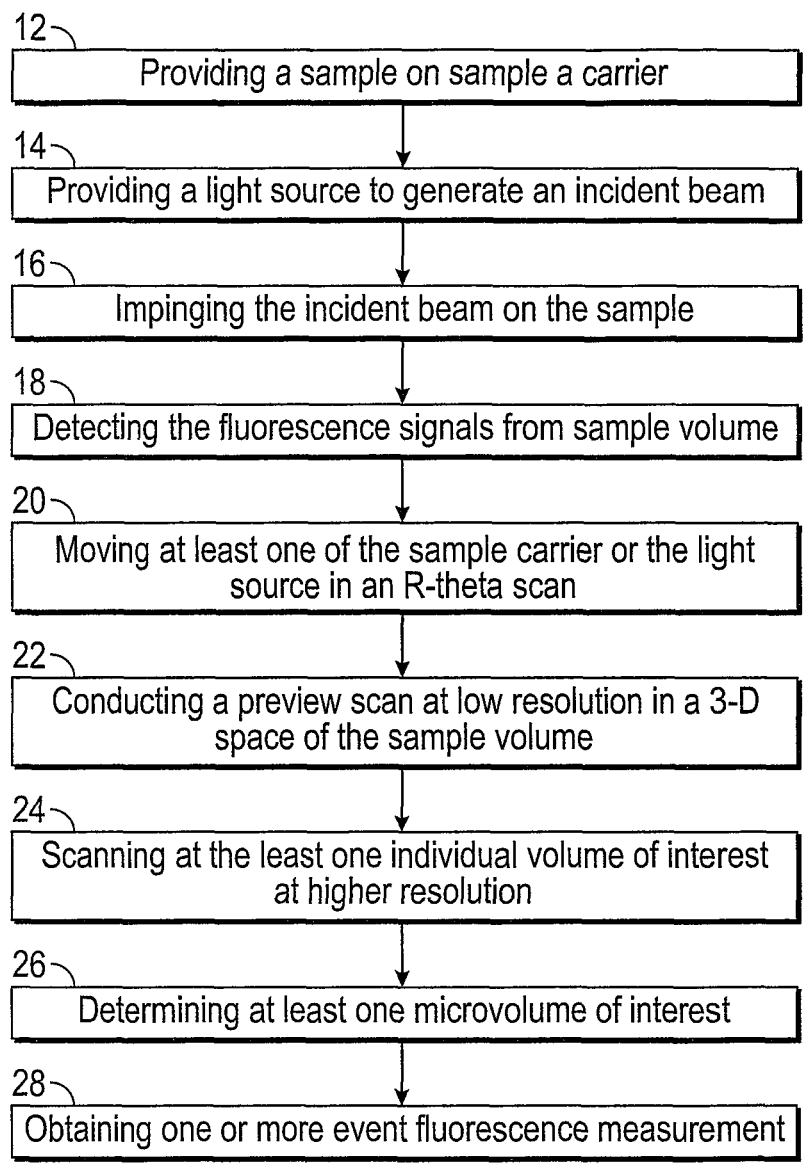
FIG. 1 is a flowchart representation of a method for measuring fluorescence according to one aspect of the invention.

As noted, in one aspect, the invention provides a method for measuring fluorescence of a sample as illustrated through flowchart 10 in FIG. 1. The method includes a step 12 for providing a sample on a sample carrier as described herein above.

The method then comprises a step 14 for providing a light source to generate an incident beam. It would be appreciated by those skilled in the art that the incident beam is characterized by a wavelength and a focus diameter. Wavelength of the incident beam useful in the invention ranges from about 300 nanometers (nm) to about 1200 nm. In one embodiment, the incident beam is a red laser beam having a wavelength that ranges from about 600 nm to about 650 nm. The implementation of a red laser source is inexpensive relative to other types of lasers. The use of a red laser source allows for the construction of a relatively inexpensive device based on the method of the invention and greater reliability of the method at ambient operating temperatures relative to other wavelengths.

As shown at step 16, the incident beam is allowed to impinge on the sample thereby causing the fluorophore portion of the sample to be excited. It may be noted that the incident beam may also sometimes be referred to as excitation beam, and the wavelength of the incident beam may be referred to as excitation wavelength. As mentioned herein the incident beam is characterized by the focus diameter, and when the incident beam impinges on the sample, the incident beam yields a laser spot that illuminates a defined volume of the sample, and described in more detail in reference to FIG. 2. The defined volume of the sample is also referred herein as a sample volume. Thus it would be appreciated by those skilled in the art that the impinging of the incident beam on the sample defines the sample volume that has a defined relationship with the focus diameter of the incident beam.

When the laser spot is focused on the sample volume, the fluorophores on the sample volume are excited giving rise to one or more fluorescence signals. The fluorescence signals of the fluorophore are generally associated with parameters such as an emission wavelength, amplitude, intensity, and the like. The fluorescence signals from the sample volume are then detected using a suitable detector as shown at step 18. In the exemplary embodiment, the choice of possible wavelengths of fluorescence signals measurable by the fluorescence detector is specifically made such that the chosen spectral region is transparent or at least minimally interfering to other components of the sample such as red blood cells that may otherwise severely interfere with the detection. Further, the choice of wavelengths of fluorescence signals allows the use of sample carriers that are made of plastic, which are significantly less expensive than those made of glass or other materials.

Figure 3:
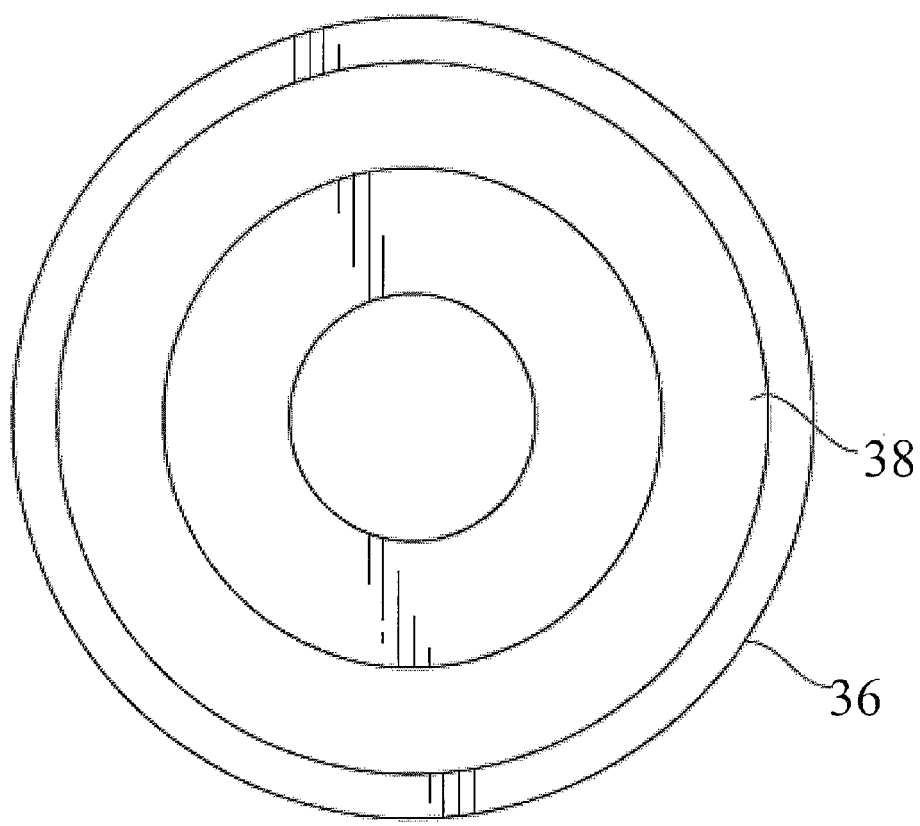
FIG. 3 is a diagrammatic representation of rotary scan obtain by moving the sample.

The method then involves moving at least one of the sample carrier or the light source or both relative to each other to scan the sample, as shown at step 20. The movement may be in any one of a linear trajectory, an arcuate trajectory or combinations thereof. In one embodiment, the light source is held stationary while the sample carrier is moved relative to the light source. Since the light source is stationary, a spiral scan of the sample carrier is achieved. In another embodiment, the sample carrier is moved in an arcuate trajectory while being simultaneously moved in a linear trajectory. The relative movement of the light source and the sample carrier is advantageous since in absence of the relative motion, the laser beam spot is relatively small to interrogate an entire fluorescing reporter of the sample in a single scan. FIG. 3 is a diagrammatic representation of a series of rotary fluorescent scans in the sample volume.

The method then includes a step 22 for conducting a preview scan at a low resolution in the manner as described herein. The preview scan, also sometimes referred to as an R-Theta scan, is conducted to define at least one individual volume of interest. This scan is also used to determine a thickness of the sample carrier based on empirical correlation between the fluorescence signals and the focus diameter. Alternately, the focus diameter may also be pre-defined to approximately match the thickness of the sample carrier. This advantageously allows for use of the sample carrier without the necessity for prior knowledge of accurate thickness value of the sample carrier.

Figure 4:
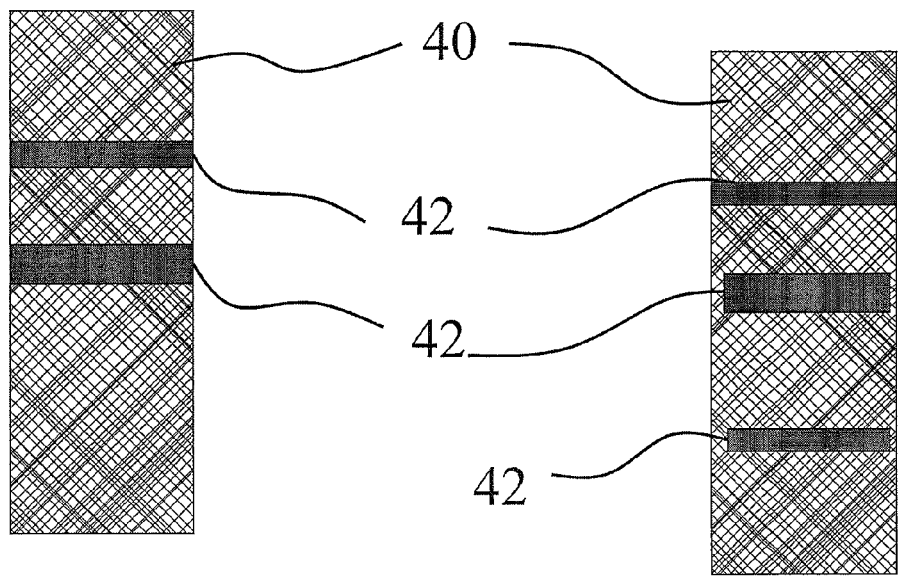
FIG. 4 is a diagrammatic representation of different microvolumes of interest within individual volumes of interest.

Without being bound to any theory, when a sample comprising at least one fluorophore is present in a sample carrier, that particular region emits higher levels of fluorescence signals relative to other regions of the sample carrier, this particular region is referred herein as individual volume of interest. The preview scan is done to define at least one individual volume of interest within the sample volume based on the one or more fluorescence signals. FIG. 4 shows a graphical representation of the sample volumes and individual volumes of interest.

In one exemplary embodiment, for a given dimension of the sample carrier and the focus diameter, the R-theta scan is conducted at a theta resolution of about 10,000 pixels per revolution and encompasses about a 3 mm wide scan (to accommodate a positional error of about +−0.25 mm) at about 50 microns spatial resolution, resulting in 60 scans. After detecting the one or more fluorescence signals, individual volumes of interest are located, and the thickness of the sample carrier is obtained as described herein above.

The preview scan also provides an opportunity to check the presence of the sample carrier, to find the approximate center of the sample carrier, confirm the proper positioning of the sample in the sample carrier, confirm the absence of bubbles, proper sample loading, and other such potential problems. Thus, the preview scan can reduce the most critical tolerance with respect to the fabrication of the sample carrier and other such manufacturing variations. This can have a measureable impact on cost reduction.

Figure 5:
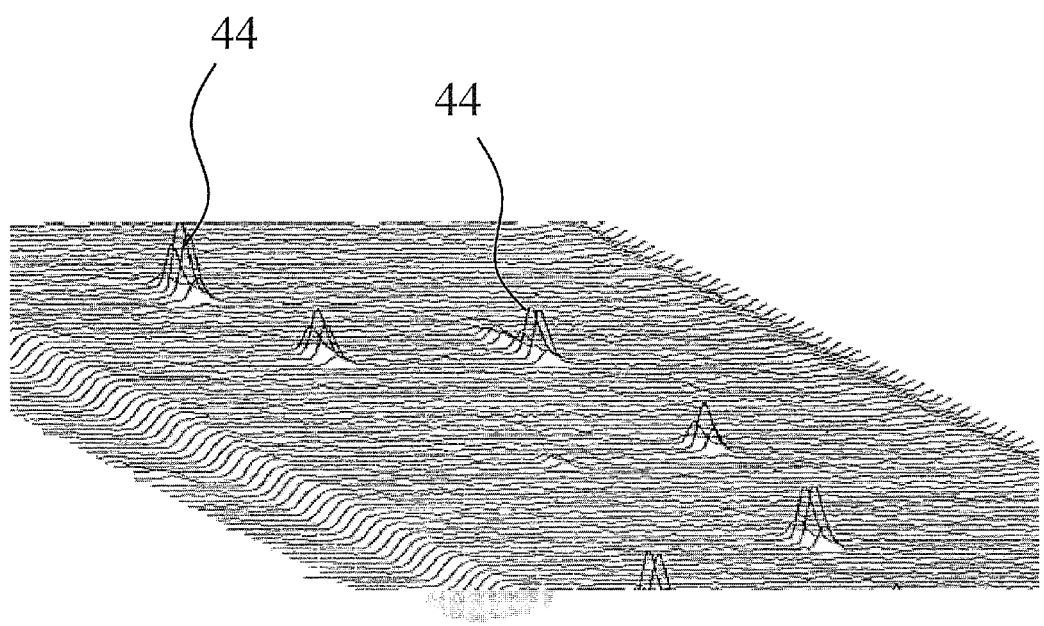
FIG. 5 is a graphical representation of fluorescence data that has been processed using a Gaussian curve-fit.

As noted herein, the R-Theta scan is used to define at least one individual volume of interest. Then, the method at step 24 includes conducting a scan at the at least one individual volume of interest at higher resolution to obtain a depth profile for the fluorophores in the sample, and also to obtain normalized bulk fluorescence measurement of the sample. It will be understood by one skilled in the art that the fluorophores may be distributed across the sample carrier. However, wherever an analyte is present, the amount of fluorophores in that region will be greater than the remaining regions. This may be due to the manner in which the sample is prepared, or through any other means known to those of ordinary skill in the art. It was observed that the optical scan of the individual volumes of interest in a sample carrier gives rise to a distribution of emitted fluorescent signals based on the presence or absence of analytes, with respect to the direction of scan. In one example, the distribution of emitted fluorescence signals was a Gaussian distribution. Thus the method involves processing the emitted fluorescence signals from the individual volumes of interest using a Gaussian curve-fitting method for each Z cross-section. The processed data in the exemplary embodiment represents Gaussian-fitted intensity maximum as a function of Theta, width of the Gaussian maximum (i.e. the measure of the capillary thickness), and the location of the Gaussian maximum along the Z-position, also referred to as depth profile. It would be appreciated by those skilled in the art that an optimum depth or Z-position is useful for the next R-theta scan to obtain event fluorescence measurements. An exemplary Gaussian curve-fitted graphical data is shown in FIG. 5.

Thus, to summarize the above steps, the scan at the at least one individual volume of interest at higher resolution is used to obtain a depth profile from the one or more emitted fluorescence signals of the at least one individual volume of interest. Further, this scan provides for a normalized bulk fluorescence measurement of the sample using the depth profile and thickness of the sample carrier.

The method then includes a step 26 for determining at least one microvolume of interest from the depth profile. As already noted herein, the region comprising the at least one fluorophore of the sample would exhibit higher intensity of one or more fluorescence signals. The microvolume of interest would typically be the region exhibiting the Gaussian maximum. Subsequently, the method includes a step 28 for focusing the incident beam on the microvolume of interest and translating the laser beam spot in the depth direction to obtain at least one concentrated emitted fluorescence signal from the at least one fluorophores present within the microvolume of interest. It would be appreciated by those skilled in the art that directing a incident beam onto the sample with a focal spot size having a generally constant diameter provides uniform illumination along the depth dimension of the sample carrier. This leads to a defined relationship of the spot size of the incident beam, and the depth dimension of the sample carrier.

The method then involves a step 28 for obtaining one or more event fluorescence measurements for the sample using the at least one concentrated emitted fluorescence signal. In one exemplary embodiment, a further R-theta scan is conducted to obtain bead and cell analysis. In another example, three or more R-theta scans were performed at the appropriate microvolume of interest. It will be understood by one skilled in the art that the different scans measured herein may be obtained by a single optical scan or it may be a composite of more than one scan. More than one scan, whether it is a R-Theta scan or a Z-Theta scan, may be conducted as the situation demands, such as when it has been determined that the whole scan sequence does not fall into one Z band due to non-flatness of the sample carrier. In an exemplary embodiment, the R-theta scan for a microvolume of interest can encompass about a 2 mm wide scan, resulting in 500 scan lines.

Figure 6:
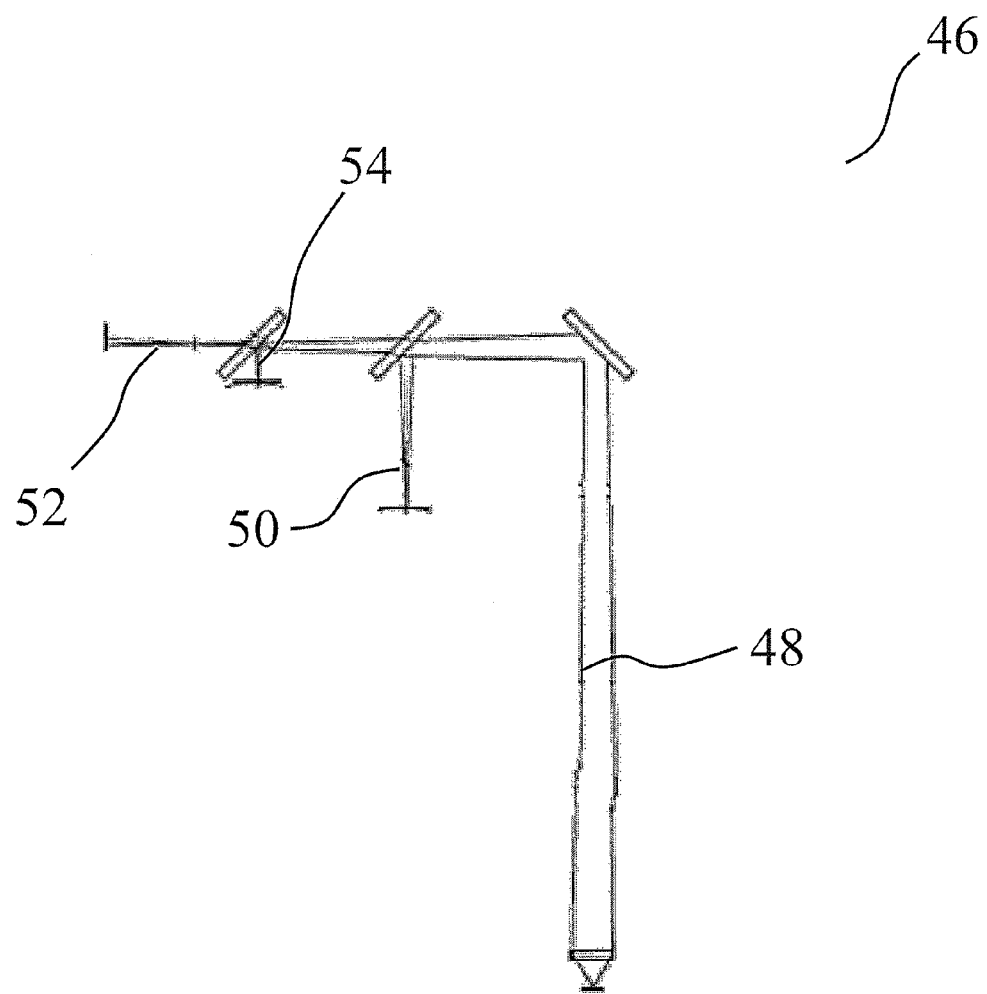
FIG. 6 shows a diagrammatic visualization of splitting of emitted fluorescence signals into three different spectral bands.

In the above described method, the detection of fluorescence signals is done at the different scanning steps 22, 24, 26 and 28. In the exemplary embodiment detection is achieved by splitting the at least one emitted fluorescence signal and the at least one concentrated emitted fluorescence signal into two or more spectral bands to enable more efficient detection. FIG. 6 shows a diagrammatic visualization of the method of detection of the at least one emitted fluorescence signals.

The method steps 22, 24, 26, and 28 also involve processing of data generated by the detection during a particular scan. In the exemplary embodiment, during an R-theta scan the data processing can include; generation of one R-theta image from a single scan or stitching together multiple Z-position level, R-theta scans, determination of the local background through pixel window spatial averaging to smooth out the effects of noise and events; subtraction of the background plus a noise floor to highlight events; using matched filter convolution to detect events; fitting a 2-D Gaussian function to characterize the events; and generating an event parameter table. At the end of any one the scanning sequences or all of the scanning sequences, an application-specific image processing software of a suitable programmable analysis device can be used to stitch or knit together all of the rotational passes over the sample to produce a final sample data image.

In general, the above described method provides high-sensitivity fluorescence measurements from relatively small samples. These attributes render the method of the invention to be adapted for use when and where critical decisions are needed to be made, such as, emergency rooms, ICUs, operating rooms, and the like. The method further allows for the elimination of the need for expensive lab infrastructures, such as air conditioning and refrigeration, allowing the delivery of diagnostic information to locations beyond labs and hospitals, including resource-poor settings.

Thus the method for measuring fluorescence as described herein advantageously provides for the simultaneous detection of normalized bulk fluorescence and event fluorescence for the sample. Similarly, a device that uses the above described method would provide for rapid and accurate analysis of samples that is inexpensive in its operation and maintenance. One skilled in the art would also appreciate the simplicity and versatility of the method as described herein above and the wide ranging applications of it. Thus, in one embodiment, the method for measuring fluorescence as described herein is used for an assay method, and in another embodiment, the method is used for an immunoassay method. Assay methods as used herein include any in vitro testing methods and in vivo testing methods. Assay methods may also include testing of substances, for example, presence of bacteria in water. Immunoassay methods as used herein include sandwich immunoassay methods, competitive immunoassay methods, and the like. In yet another embodiment, the method for measuring fluorescence as described herein is used for cell and bead assay methods. In a further embodiment, the method of the invention is used for chemical detection, such as explosive detection, drug detection, and the like. In yet another alternate embodiment, the method for measuring fluorescence as described herein is used for flow cytometry assay. Currently, different devices are used for the different applications enumerated herein, whereas the method for measuring fluorescence as described herein provides the capability of having a single device based on the method of the invention that can be used for all of the various applications described herein.

FIG. 2-FIG. 6 described herein below represent different aspects of the method of FIG. 1.

Figure 2:
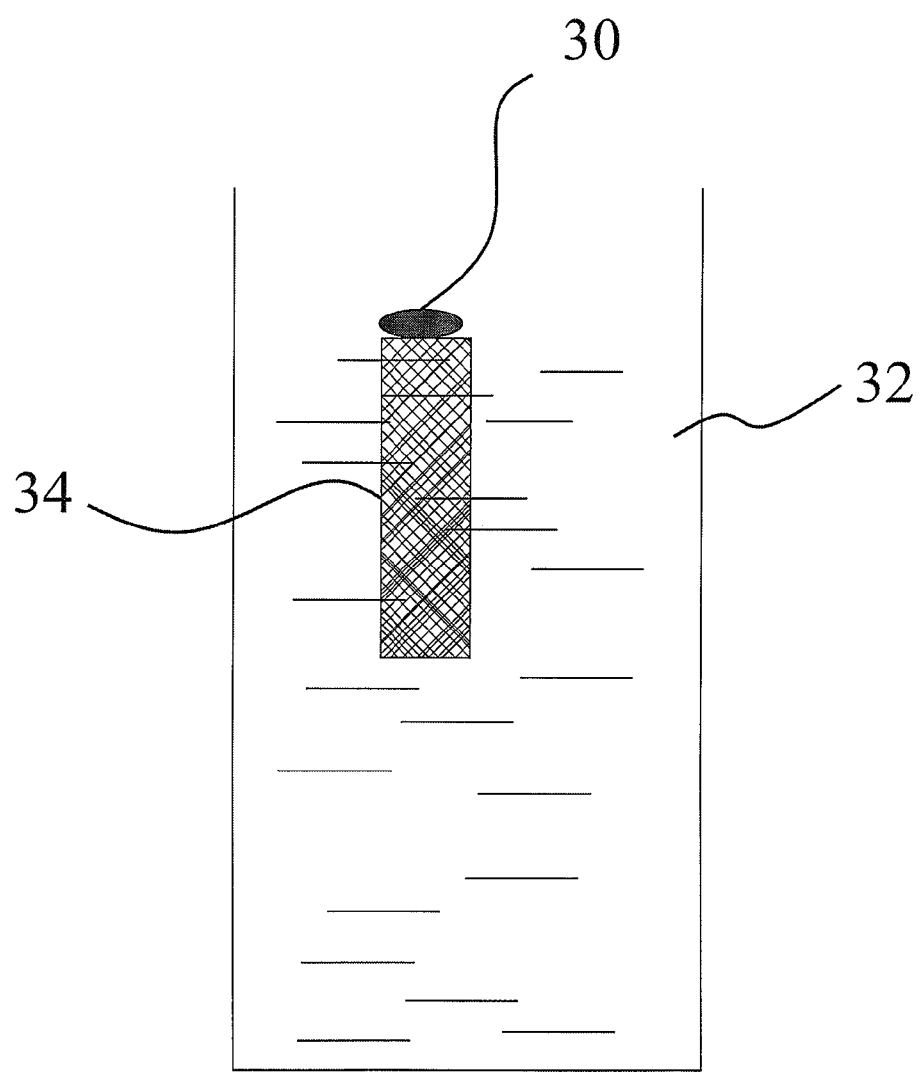
FIG. 2 is a diagrammatic representation of a laser spot and an individual volume of interest.

FIG. 2 is a diagrammatic representation of the laser spot 30 that illuminates a portion of the sample 32 that is present on a sample carrier, referred herein as sample volume 34. It would be appreciated by those skilled in the art that the sample volume is a geometrical region comprised within the sample, the exact shape of the region depends on several factors, such as, but not limited to, thickness of the sample carrier, shape of the sample carrier, refractive index of the sample medium, material making up the sample carrier, and the like. FIG. 2 shows one exemplary embodiment, wherein the sample volume is viewed as a cylindrical region.

FIG. 3 is a diagrammatic representation of rotary scans as mentioned herein in reference to FIG. 1. As mentioned herein above, by moving the sample carrier 36 linearly, while continuously scanning in a rotary manner, results in a series of rotary fluorescent scans through the sample volume, an annular area 38 of the sample carrier 36. Such spiral scans ensure that all fluorophores of the sample are interrogated during a scanning sequence. The advantage of holding the light source and related optics part stationary during the scanning process is that it will result in a low-cost diagnostic system that uses the method of the invention. Further, the ability to continuously scan in a spiral orientation achieves high-precision fluorescent measurements. The moving of the sample carrier in a linear and an arcuate trajectory simultaneously can be achieved using methods known in the art. In one exemplary embodiment, the moving of the sample carrier is achieved using a stepper motor.

FIG. 4 shows a graphical representation of the sample volumes 40 and individual volumes of interest 42 as described in reference with FIG. 1.

FIG. 5 shows an exemplary Gaussian curve-fitted graphical data 44 as described in reference with FIG. 1.

FIG. 6 shows a diagrammatic visualization of the method of detection 46 of the at least one emitted fluorescence signals as described in reference to FIG. 1. In one embodiment, each of the at least one emitted fluorescence signal 48 (shown here as double beam from the sample) is split into a first spectral band 50, a second spectral band 54 and a third spectral band 52. In one example, the first spectral band has a wavelength that ranges from about 650 nm to about 690 nm, the second spectral band ranges from about 690 nm to about 740 nm, and the third spectral band ranges from about 740 nm to about 800 nm. The splitting of the fluorescence signals into spectral bands may be achieved in a facile manner using a suitable device such as beam splitter.

Figure 7:
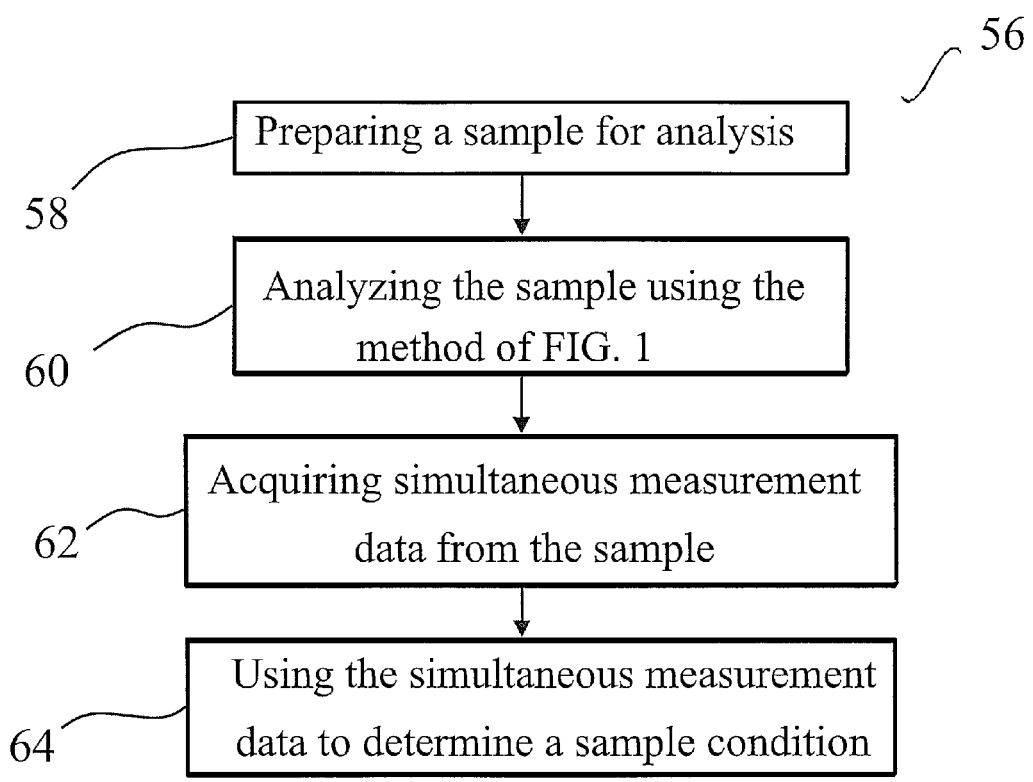
FIG. 7 is a flowchart representation of method for analyzing a sample according to aspects of the invention.

In another aspect, the invention provides a method for the analysis of a sample as represented by flowchart 56 in FIG. 7. The method of analysis comprises a step 58 for preparing a sample for analysis, wherein the sample comprises at least one fluorophore. Sample preparation may involve techniques described herein, such as, for example, adding an aliquot of blood to a reagent that comprises a fluorophore. Further, after the addition of the fluorophore, a separate step may be included to ensure adequate mixing and reaction of the reagent with blood. Exemplary techniques may include mixing, shaking, vortexing, and the like, and is known to those of ordinary skill in the art.

After preparing the sample, as indicated at step 60, it is analyzed using the method of FIG. 1 as described herein, which leads to step 62 for acquiring simultaneous measurement data from the sample. The simultaneous measurement data as used herein means any data that is representative of one or more fluorescence events for at least one individual volume of interest and the normalized bulk fluorescence for the sample. In one exemplary embodiment, the simultaneous measurement data includes the detection of the presence or absence of an antigen associated with an antibody. In another exemplary embodiment, the simultaneous measurement data includes the detection of presence or absence of microorganism contamination in water. In yet another exemplary embodiment, the simultaneous measurement data includes the quantification of amount of glucose present in a blood. In a further exemplary embodiment, the simultaneous measurement data includes detection of the presence or absence of a narcotic in a urine sample.

As an illustration, in the case of acquiring of simultaneous measurement data for the quantitation of CD-4. Sample is treated with an appropriate set of antibodies such as, MAH anti-CD4 antibody that binds to the CD-4, which is then linked to a fluorophore by mixing it with an appropriate reagent for a period of time with agitation. This is then subjected to the method of invention. Based on the intensity of the fluorescence signals arising out of the prepared sample, the amount of CD-4 cells may be quantified.

The method of analyzing a sample may further include a step 64 for using the simultaneous measurement data to determine a sample condition. In one example the sample condition may be an analyte measure. Analyte measure may include identifying the presence or absence of an analyte, or it may include quantification of an analyte in the sample. The analyte measure may also be to determine a quality of a sample, such as quality of water in a region to determine if the water is potable, for example. In another example sample condition may be a disease condition. For example, the amount of CD-4 cells measured may be used to determine the susceptibility of a patient to any immunodeficiency related afflictions, and also towards making decisions towards starting treatment for such afflictions. Similarly, the simultaneous measurement data may be used to quantify the blood glucose concentration. Based on the blood glucose concentration, the determination of a disease condition, namely, diabetic or not, can be made.

Further, the determination of the disease condition may be made to determine a course of a suitable treatment. This may include administration of drugs such as insulin to the patient, the dosage being determined based on several factors such as, but not limited to, medical history, medical condition, diet, weight, physical condition, and the like. The disease condition may further be classified as being one of onset, a progression, a regression, stable, and an advanced condition.

Figure 8:
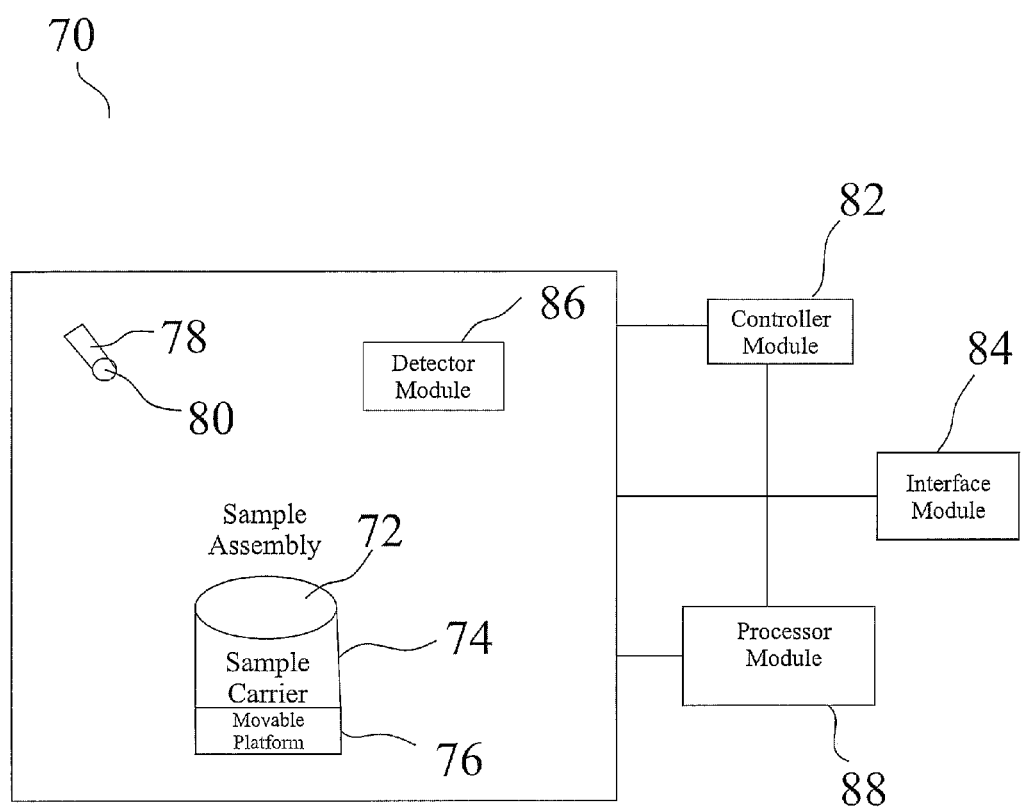
FIG. 8 is a diagrammatic representation of an exemplary embodiment of a device for measuring fluorescence according to aspects of the invention

In yet another aspect, the invention provides a device that is based on the method for measuring fluorescence as described herein above. FIG. 8 is a block diagram representation for an exemplary embodiment of the device 70. The device 70 includes a sample assembly 72 for receiving a sample carrier 74 that comprises a sample, wherein the sample comprises at least one fluorophore. The sample carrier may be any one of a channel, well, capillary, membrane, and combinations thereof. The sample carrier has a predefined region to receive the sample. Sample assembly may comprise a plurality of sample carriers, wherein all the sample carriers comprise a sample or only a few sample carriers comprise sample while the remaining are empty during operation of the device of the invention. In some instances, different samples may be provided in different sample carriers. Sample may be prepared in situ in the sample carrier or it may be prepared separately and then added into the sample carrier. Adding a prepared sample into the sample carrier may be achieved by known means, such as for example pipetting. The nature of the sample carrier may be specific for a particular application, the choice of which will be obvious to one of ordinary skill in the art. In one exemplary embodiment, the sample carrier is a cuvette, and in another exemplary embodiment, the sample carrier is a capillary.

The sample assembly further includes a movable platform 76 configured in such a way that it can be attached to the sample carrier through a suitable locking means. Locking means are known to those of ordinary skill in the art, and may include fasteners, mechanical means, magnetic means, and the like. In one embodiment, the locking means is by magnetic means. In this situation, a magnetic material is present on at least part of the sample carrier, and a magnetic material of the opposite polarity and suitable magnetic strength at the complementary position of the movable platform. This will ensure that when the two components are brought together, they will be held strongly in place through magnetic attraction forces.

The movable platform in the sample assembly is further capable of being moved in a suitable trajectory. The movement may be achieved by the use of a stepper motor, the mechanism of which is known in the art. The movable platform is capable of being moved in a linear trajectory, an arcuate trajectory, or both. In one embodiment, the movable platform is capable of being in both a linear and an arcuate trajectory. In one embodiment, the movable platform is controlled using a stepper motor. Other useful components that can be used as part of the sample assembly will become obvious to one skilled in the art.

The device 70 includes a laser subsystem 78 that comprises a light source 80. The light source provides an incident beam that is impinged on the sample. In a typical use scenario, when the movable platform moves, the entire sample assembly moves. When the incident beam is allowed to impinge on the sample, the movement of the sample assembly causes different portions of the sample to be illuminated by the incident beam, giving rise to space-dependent fluorescence signals including emitted fluorescence signals as mentioned in reference with FIG. 1.

When the sample present on a movable platform is moved in a linear and an arcuate trajectory, a spiral scan of the sample by the laser beam spot is achieved. The speed of rotation of the sample assembly and the linear movement will vary depend on the nature of analysis being performed, and can be controlled using a controller module 82. The manner in which the speeds are input to the device 70 may vary, it may be through re-defined speed settings or may depend on the skill of the user, the expertise and experience, and such other factors. Thus, in one embodiment, the speeds are input through an interface module 84, while in another embodiment, the choice of a particular type of analysis from a menu in a graphical user interface module 84 will automatically select the speeds of the sample assembly. It may be understood by those skilled in the art that other displacement means replacing or in combination of the movable platform may be provided for displacing the laser spot relative to the sample volume in a three dimensional space defined by the sample volume, wherein the sample volume comprises at least one individual volume of interest. The resulting emitted fluorescence signals are detected as described herein.

As described herein above, the impinging incident beam will cause excitation of the fluorphores on the sample, giving rise to emitted fluorescence signals. These emitted fluorescence signals are then detected using detector module 86 using techniques as described in reference to the method of FIG. 1. The detection scheme in an exemplary embodiment involves splitting the emitted and concentrated fluorescence signals into different spectral bands, where each spectral band has a specific wavelength range. Thus, a set of event fluorescences may be obtained from the sample.

The device 70 includes a processor module 88 for estimating a depth profile and a thickness of the sample. carrier from the one or more emitted fluorescence signals, wherein the depth profile comprises the at least one individual volume of interest. The processor module 88 is configured to use the depth profile and the thickness for measuring normalized bulk fluorescence for the sample. The processor module 88 is further configured to determine at least one microvolume of interest from the depth profile using the detected fluorescence signals. The controller module 82 is also used to trigger the light source to focus the incident beam on the microvolume of interest to obtain at least one concentrated emitted fluorescence signal.

The processor module 88 may be used to measure one or more event fluorescences for the sample based on the detector signals from the microvolume of interest. The manner of converting the detector signals into measurable parameters such as quantitative outputs, graphical outputs, and the like is known to one skilled in the art.

Figure 9:
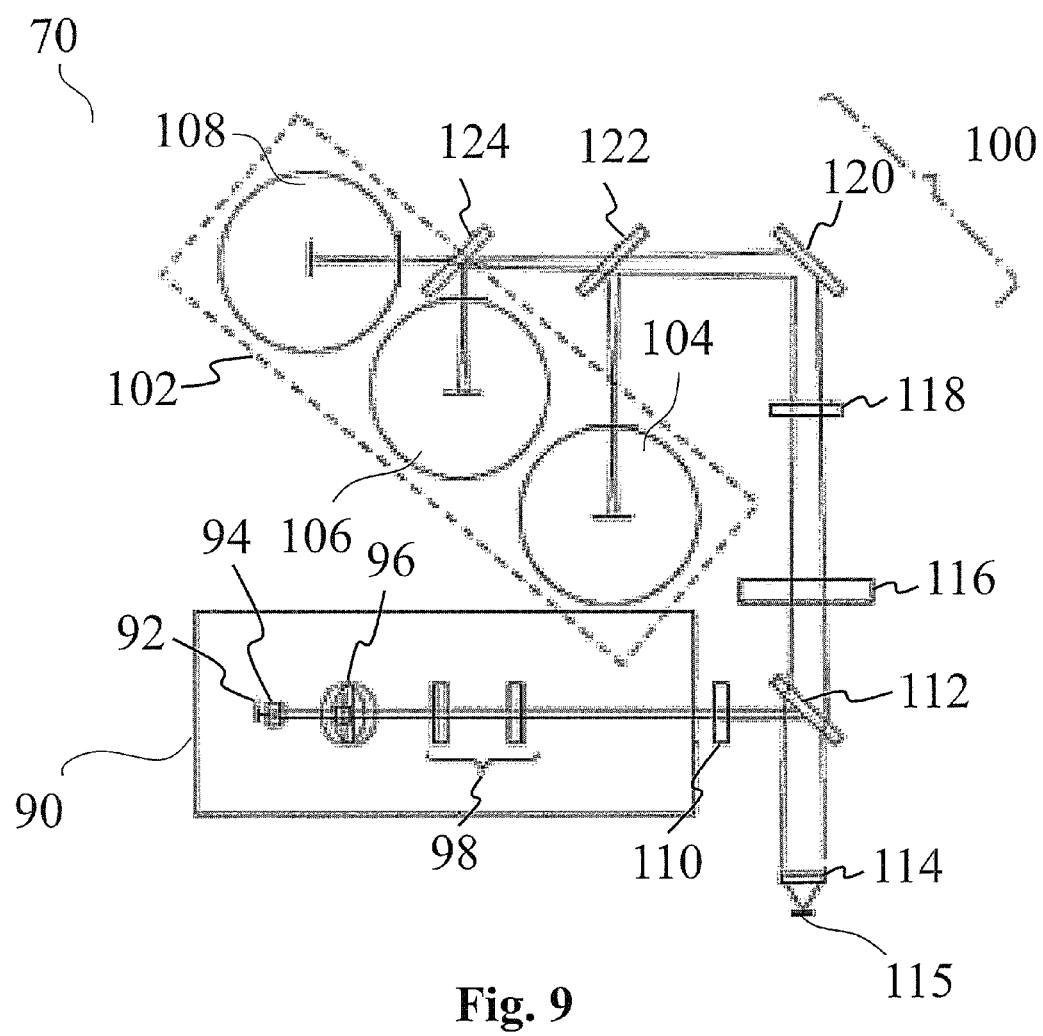
FIG. 9 is a diagrammatic representation of another exemplary embodiment of the device of FIG. 8.

FIG. 9 shows another exemplary embodiment of the device 70, which comprises the laser subsystem 90 that includes a light source e.g. a red laser diode 92 for generating an incident beam having an excitation wavelength and a focus diameter to impinge on the sample to yield a laser spot that defines a sample volume for measuring fluorescence. The excitation wavelength useful in the invention ranges from about 600 nm to about 800 nm. In one embodiment, the excitation wavelength is about 640 nm. The device of the invention may include, besides a red laser diode 92, a laser lens 94, a tilted glass plate 96, and a series of cylindrical lenses 98. As set forth above, the red laser diode 92 of the laser module subsystem 90 can emit a red laser beam most preferably at about 640 nm, but could be in the range from about 600 nm to about 800 nm. The emitted beam can then be directed through the laser lens 94 which collimates the light coming out of the laser diode 92. The collimated light is then directed to the tilted glass plate 96 which can act to translate the beam along the x and y axes thereby tilting the beam slightly as desired. Afterwards, the laser beam can be directed through the series of cylindrical lenses 98 which can expand the beam in one direction to change it from an elliptical shape (as it was emitted from the laser diode 92) to a preferred quasi-circular shape. The laser module subsystem 90 is capable of emitting an excitation laser beam which can eventually form a focused laser spot having a generally constant diameter on the sample. Thus, the impinging incident beam on the sample defines a sample volume that has a predefined relationship with the focus diameter.

The laser module subsystem 90 can also include a power detector (not shown). The power detector is arranged to receive a portion of the laser beam which is split off by way of, for example, the tilted glass plate 96. The power detector can monitor the power of the laser beam and feed a signal back to the laser diode 92 in order to stabilize the output of the laser diode 92 such that it emits a consistent amount of light.

The quasi-circular laser beam emitted out of the laser module subsystem 90 is then directed through the focusing and signal collection optics with scanner subsystem 100. This subsystem 100 can include a series of lenses, mirrors, filters, and the like which are arranged in a manner to direct the red laser beam onto the sample to be analyzed, and then direct the resulting emitted fluorescent signal against a series of photomultipliers (PMTs) 104, 106, 108 making up the photodetector subsystem 102.

In this regard, the subsystem 100 can include a laser filter 110 which acts to clean up the beam that is emitted from the laser subsystem 90. The laser filter 110 cleans the beam such that only laser light is directed against the sample. The beam can then be directed against a beam splitter 112 which operates to reflect the laser beam onto the sample. The reflected laser beam is directed through a focusing lens 114 which concentrates the beam onto the sample 115 with a spot size having a generally constant diameter.

The fluorescent signal emitted from the sample 115 (including emitted and concentrated fluorescence signal described herein above) then passes through the beam splitter 112 and is then directed through a laser rejection filter 116. The laser rejection filter 116 acts to block any laser light from being transmitted further downstream. The emitted fluorescent signal is then directed through a focal lens 118 which operates to focus the signal on the photomultipliers (PMTs) 104, 106, 108 of the detector subsystem 102. Downstream of the focal lens 118 is a folding mirror 120 which directs the signal toward two beam splitters 122, 124. First beam splitter 122 is designed to reflect a signal in the range of about 650 nm to about 690 nm against the first PMT 104. Second beam splitter 124 is designed to reflect a signal in the range of about 690 nm to about 740 nm against the second PMT 106, while allowing a signal above about 750 nm to pass through to the third PMT 108.

Accordingly, the detector subsystem 102 can include a series of photosensitive detectors or PMTs 104, 106, 108 all of which can read in the red and near infrared region. These PMTs, along with the components of the focusing and signal collection optics 100, provide the ability to divide a fluorescent signal emitted from the sample into different spectral regions or channels. In this manner, experiments can be conducted simultaneously on a single sample through the use of a number of specific reagents for each desired experiment, thereby achieving a multiplexing capability. For example, a first reagent can be added that emits a fluorescent signal that can be divided and then read by the first PMT 104, a second reagent can be added that emits a fluorescent signal that can be divided and then read by the second PMT 106, and so on. In this manner, a single laser beam emitting at a particular wavelength (e.g. 640 nm) can be designed to excite a plurality of fluorophores, each of which then each emits at a number of different fluorescent wavelengths.

According to various embodiments, additional PMTs can be implemented into the detector subsystem 102, or stacked onto a secondary detector subsystem (not shown) which can also be arranged to read an emitted and concentrated fluorescent signal from the sample. In this manner, additional experiments could be conducted by way of the addition of additional fluorophores as well as additional laser diodes.

Such an optically-defined volume measurement facilitates the measurement of the concentration of fluorescing particles within a predefined volume (which is relatively small) and not the total fluorescence of the entire sample (a large volume). As a result, fluorescent measurements can be taken using the device 70 without needing to know the total volume of the sample being measured, since the volume over which the measurement is taken is known due to the well-defined, focused laser beam spot. The incorporation of such an optics arrangement is advantageous as it precludes the necessity of knowing the control path length of the sample assembly, thereby allowing the manufacture of cost-effective sample carriers, as well as the sample assembly in general.

Figure 10:
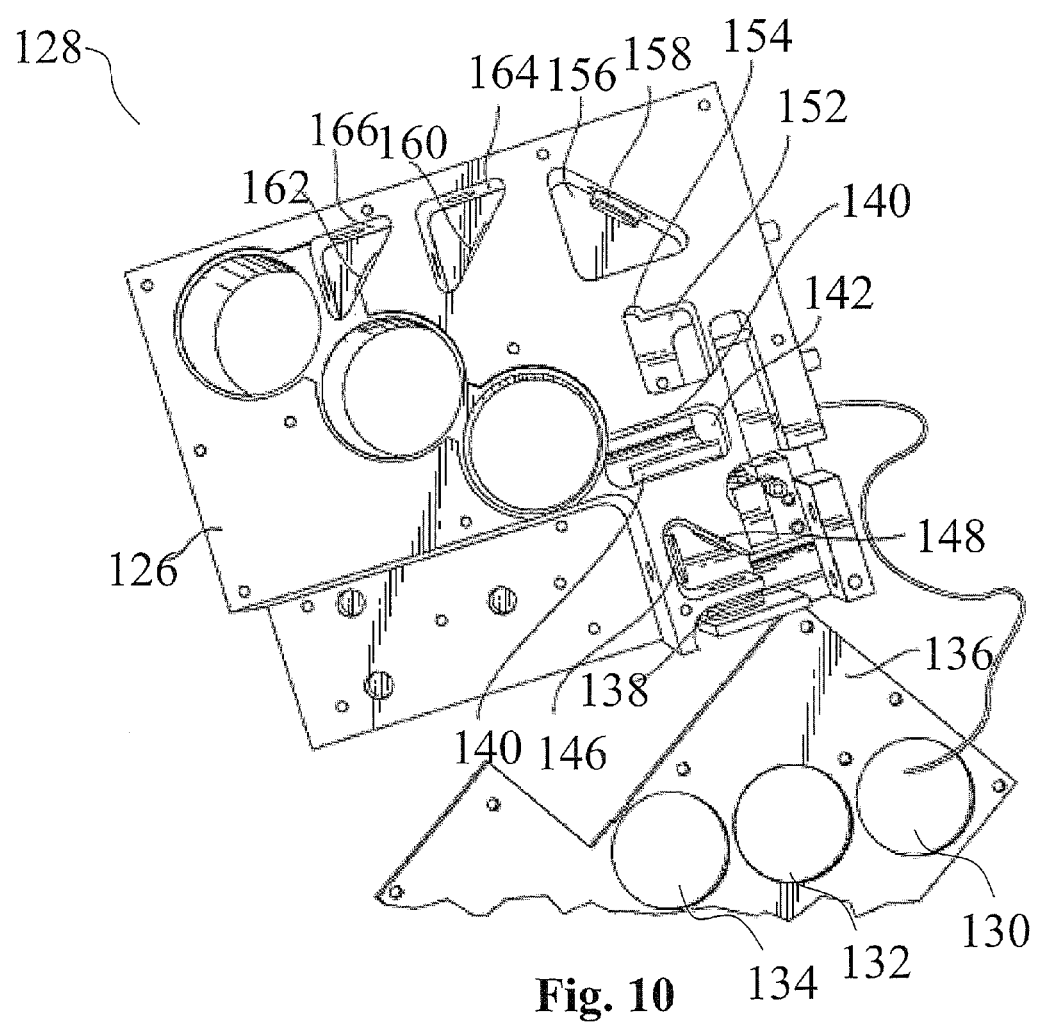
FIG. 10 is a diagrammatic representation of yet another exemplary embodiment of the device of FIG. 8.

FIG. 10 shows another exemplary embodiment of the device showing the components of the stationary optics module 128, which has further added features and components built into it, such as a base plate or platform 126 with the PMTs 130, 132, 134 and a cover plate 136 removed. In one example, the base plate 126 can be formed with three holes into which the PMTs 130, 132, 134 can be installed, and if necessary, more holes may be drilled into it to include more PMTs. The focusing lens 138 is shown movably secured to the base plate 126 for vertical focusing movement. Laser rejection filter 140 for filtering the laser beam going into the system is shown secured vertically within a compartment 142 formed in the base plate 126.

The laser beam generated by the laser module subsystem (not shown here) can be directed through an aperture formed in the base plate 126 after which the laser beam is directed through the laser filter 146. In the same compartment, the beam splitter or folding mirror 148 can be arranged which operates to reflect the laser beam downwardly onto the focusing lens 138, as well as transmitting the emitted fluorescent signal therethrough into the next compartment 142 by way of a further aperture formed in the base plate 126. Secured to a wall of compartment 142 is the laser rejection filter 140 which only passes an entering emitted fluorescent signal while rejecting any laser light. The cleaned emitted fluorescent signal can then be directed through further apertures into a downstream compartment 152. A slot can be formed within a wall of compartment into which the focusing lens 154 is secured.

After passing through focusing lens 154 and an aperture connecting compartment 152 with compartment 156, the emitted fluorescent signal can be reflected by folding mirror 158 arranged in compartment 156 in a direction toward the first beam splitter 160 and the second beam splitter 162 through corresponding apertures in the base plate 126. The first beam splitter 160 can be secured in compartment 164 and includes apertures which allow any reflected emitted fluorescent signal to be reflected downwardly to the first PMT 130. The second beam splitter 162 can be secured in compartment 166 and can include apertures which allow any reflected emitted fluorescent signal to be reflected downwardly to the second PMT 132. An additional aperture can be provided in compartment 166 which allows any emitted fluorescent signal not reflected by either beam splitters 160, 162 to be directed toward third PMT 134.

Each of the disclosed lenses can be secured to the base plate 126 by way of an adhesive or any known way as would be appreciated in the art, such as by way of fasteners and the like.

The measurement capabilities of the device 70 as described in different embodiments herein above allow for the performance of diagnostic tests that have been typically done using several different instruments in a clinical diagnostic laboratory, including clinical chemistry, immunology, and cytometric assays. More particularly, the device 70 can perform various complex assays including: clinical chemistry and microbiology assays, immuno-assays (including sandwich immuno-assays and competitive immuno-assays), bead and cell enumeration assays, cytometry, cell activation and cell expression assays, and various others.

The device 70 may further be connected to a programmable analysis device, such as a laptop computer and the like. The programmable analysis device can be programmed to control the operation of the device 70, to receive sample data transmitted from the device 70, and to analyze the sample data using computerized software algorithms. For example, the programmable analysis device can be programmed to control the device such that a specific scanning sequence is performed based on the type of sample carrier to be loaded onto the device 70. The programmable analysis device can be arranged to interface with the device 70 by way of a wired and/or a wireless communication protocol.

Figure 11:
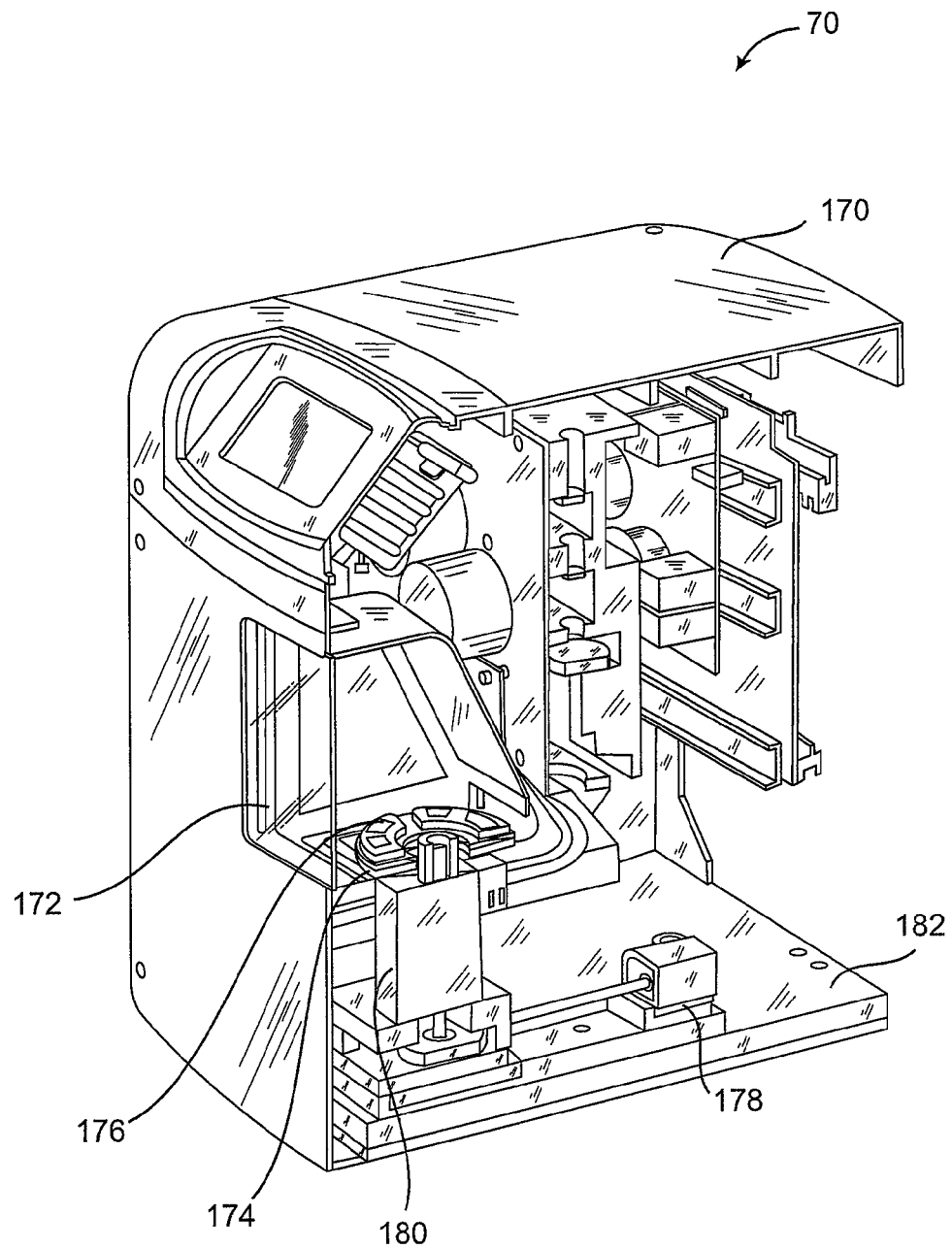
FIG. 11 is a diagrammatic representation a further exemplary embodiment of the device of the invention.

FIG. 11 shows a further exemplary embodiment of the device 70, which comprises further useful components to impart further useful capabilities to the device. The device 70 comprises a housing unit 170, wherein the device is useful as a tabletop diagnostics unit. For example, the dimensions of the housing unit 170 can be about 10" wide, by about 10" deep, by about 12" high, but other dimensions could be implemented, as would be appreciated by one of ordinary skill in the art. The housing unit 170 can include a door 172 which can be opened and closed to allow user access to the sample assembly 174. Access to the sample assembly 174 allows a user to insert, remove, and/or replace sample holder 176 from the device 70. The movement of the sample assembly is controlled by a rotary stepper motor 178 and a linear stage stepper motor 180 to effect translation of the sample assembly in a linear trajectory and an arcuate trajectory.

It may be further appreciated by those skilled in the art that the device 70 in an exemplary implementation, obviates the need for a cooling fan, that is usually necessary in such devices. This is due to the low power consumption of the device. In the exemplary implementation, the maximum power consumption was about 15 W. The device 70 can also be programmed to turn-off certain non-critical components of the device 70 during use, or while in a stand-by mode. As a result, even if the device 70 is run all day, it advantageously prevents build-up of a significant amount of heat. Notwithstanding, to dissipate any accumulation of heat, the stepper motors can be provided with cooling fins so as to reduce heat transfer to an assay application cartridges 28 as much as possible. Moreover, vents could be incorporated into the platform base 182, as well as into the top of the housing unit 170 to allow natural convection cooling of the device 70. If vents are incorporated, a filter system could also be implemented to prevent dust and other unwanted particles from entering into the interior of the detection device 70.

In a further aspect, the invention provides a system that uses the device of the invention, which in turn is based on the method of the invention.

EXAMPLES

In one illustrative embodiment for the preparation of a sample for conducting a clinical chemistry measurement, a sample of whole blood is taken from a patient and at least one enzyme is added to the blood sample depending on the protein or compound being tested for. The addition of the at least one enzyme results in a reaction that produces $H_2O_2$, Alkaline Phosphate, or NAD-NADH depending on what is being tested for and whether it is present in the blood sample. The fluorophores are then added to the mixture and will create a fluorescently-tagged mixture in the presence of $H_2O_2$, Alkaline Phosphate, or NAD-NADH in the blood sample.

The device 70 as described herein is used to conduct enzyme-linked immunosorbent assay (ELISA). In conducting ELISA, a surface of an assay sample carrier is prepared, such as a plate-like surface of a channel, capillary, well, or any readable portion of the sample carrier. A known quantity of a capture antibody is then bound to this surface. Any non-specific binding sites on the prepared surface are then blocked. Afterwards, an antigen-containing blood sample is applied to the plate-like surface of the sample carrier. The plate-like surface is washed so that any unbound antigen is removed. Primary antibodies that bind specifically to the antigen in the blood sample are then applied to the sample carrier. Enzyme-linked secondary antibodies which are specific to the primary antibodies are then also applied. The plate-like surface is washed so that the unbound antibody-enzyme conjugates are removed. Substrates are then applied which are converted by the presence of an enzyme into an emitted fluorescence signal. The fluorophores are designed to fluoresce in the far red and near infrared region when excited by the red laser of the device 70.

The sample carrier can be loaded onto the sample assembly of the device 70 which conducts a rotary scan using the red laser of the device 70. Sample data is processed to create an image in the manner as discussed above. In this manner, ELISA can be conducted using the device 70.

The device 70 can be used to conduct fluorescent bead-based immuno-assays. In conducting such assays, a plurality of fluorescent beads which have been coated with a capture antibody, in addition to a secondary antibody which has been conjugated with fluorophores, can be pre-formulated, unitized, and dried within a small sample tube. The fluorophores which have been conjugated with the secondary antibody can be those, as discussed above, that are designed to fluoresce in the far red and near infrared region when excited by the red laser of the device 70.

When a user is ready to conduct an immuno-assay of a blood sample, a measured volume of the blood sample can be added to the sample tube by way of a pipette or similar device. The addition of the blood sample operates to reconstitute the formulation within the sample tube. The resulting mixture can then be incubated for a predetermined period of time, such as, for example, about 30 minutes. The incubation time is dependent on the affinity characteristics of the antibody used and the concentration of the antigen. A diluent can then be added to the sample tube and mixed for a period of time, such as, for example, several seconds.

The resulting diluted mixture in the sample tube are then delivered onto one or more micro-wells, or onto the membrane material of a sample carrier, where fluorescence measurements among a plurality of spectral channels can be conducted using the device 70. For example, fluorescence measurements can be made of i.) the secondary antibody attached to the fluorescent beads in a first spectral channel, ii.) the fluorescent beads in a second spectral channel, and iii.) a reference protein having a reporter fluorescence in a third spectral channel which can act as an internal control. In this manner, fluorescent bead-based assays can be conducting using the device 70.

While only certain features of the invention have been illustrated and described herein, many modifications and changes will occur to those skilled in the art. It is, therefore, to be understood that the appended claims are intended to cover all such modifications and changes as fall within the true spirit of the invention.

I claim:

1. A method for measuring fluorescence comprising:
providing a liquid sample having a volume contained in a sample carrier, wherein the sample volume contains at least one fluorophore amidst bulk fluorescence of the sample;
providing a laser light source to generate a scanning spot of a single wavelength having an excitation wavelength and a focus diameter to impinge on the sample volume for measuring fluorescence; and
displacing the laser spot of said single wavelength, relative to the sample volume, with a two dimensional preview scan, by moving the sample carrier and the incident beam relative to each other in an R-theta scan at a first resolution to detect in a three-dimensional space, defined by the sample volume, at least one individual volume of interest where fluorescence exceeds bulk fluorescence in other regions of the sample carrier wherein the at least one volume of interest and the laser spot have a defined relationship, then
measuring a depth profile of fluorescence in the at least one individual volume of interest at a second resolution higher than the first resolution as a profile of the at least one fluorophore therein amidst the bulk fluorescence,
wherein a two dimensional R-theta scan of the sample at a single wavelength establishs three dimensional fluorescence profiles of the at least one fluorophore in the sample amidst the bulk fluorescence.

2. The method of claim 1 further defined by obtaining the thickness of the sample carrier, wherein the depth profile and the thickness are used for measuring normalized bulk fluorescence.

3. The method of claim 1 further comprising:
determining at least one microvolume of interest from the depth profile; and
focusing the incident beam on the microvolume of interest to obtain at least one concentrated emitted fluorescence signal.

4. The method of claim 3, wherein the at least one concentrated emitted fluorescence signal is used to measure one or more event fluorescences for the sample.

5. The method of claim 3, wherein the one or more emitted fluorescence signals and the at least one concentrated emitted fluorescence signal are split into two or more spectral bands.

6. The method of claim 3, wherein the one or more emitted fluorescence signals and the at least one concentrated emitted fluorescence signal are split into a first spectral band, a second spectral band and a third spectral bands.

7. The method of claim 6, wherein the first spectral band ranges from about 650 nm to about 690 nm, the second spectral band ranges from about 690 nm to about 740 nm, and the third spectral band ranges from about 740 nm to about 800 nm.

8. The method of claim 1, wherein the excitation wavelength ranges from about 300 nanometers to 1200 nanometers.

9. The method of claim 8, wherein the excitation wavelength ranges from about 600 nanometers to 650 nanometers.

10. The method of claim 9, wherein the excitation wavelength is about 640 nanometers.

11. The method of claim 3 further comprising:
measuring a normalized bulk fluorescence using the depth profile and the thickness of the sample carrier; and
measuring one or more event fluorescences for the sample using the at least one concentrated emitted fluorescence signal.

12. The method of claim 1, wherein the at least one individual volume of interest and the spot created by the incident beam have a defined relationship in the R-theta scan.

13. The method of claim 1, wherein the moving in the R-theta scan is in a linear trajectory and an arcuate trajectory combined.

14. The method of claim 3, wherein the excitation wavelength ranges from about 300 nanometers to 1200 nanometers.

15. The method of claim 3, wherein the excitation wavelength ranges from about 600 nanometers to 850 nanometers.

16. The method of claim 15, wherein the excitation wavelength is about 640 nanometers.

17. A fluorescence measuring device comprising:
a sample assembly for receiving a sample carrier that comprises a sample, wherein the sample comprises at least one fluorophore amidst background bulk fluorescence;
a laser light source for generating an incident beam having a single excitation wavelength and a focus diameter to impinge on the sample to yield a spot for measuring fluorescence;
a means for displacing the spot in a two dimensional low resolution scan relative to the sample volume in a three dimensional space by moving the sample carrier and the incident beam relative to each other in an R-theta scan, the three dimensional space including mostly bulk fluorescence; and
a means for detecting at least one individual volume of interest in the two-dimensional low resolution scan that has the at least one fluorophore amidst background bulk fluorescence therin, wherein the at least one individual volume of interest and the laser spot have a defined relationship, then displacing the spot in a high resolution scan to measure the depth profile of fluorescence in the volume of interest as a profile of the least one fluorophore in background bulk fluorescence,
wherein a two-dimensional scan of the sample establishes three dimensional fluorescence profiles of the at least one fluorophore amidst the background bulk fluorescence.

18. The device of claim 17 further comprising a processor module for obtaining a depth profile and a thickness of the sample carrier from the one or more emitted fluorescence signals, wherein the depth profile is in the at least one individual volume of interest.

19. The device of claim 18, wherein the processor module uses the depth profile and the thickness for measuring normalized bulk fluorescence.

20. The device of claim 18, wherein the processor module is configured to determine at least one microvolume of interest from the depth profile.

21. The device of claim 20 further comprising a controller module to trigger the light source to focus the incident beam on the microvolume of interest to obtain at least one concentrated emitted fluorescence signal.

22. The device of claim 17, wherein the at least one individual volume of interest and the spot have a defined relationship.

23. The device of claim 21, further comprising a detector assembly to detect the one or more emitted fluorescence signals and the at least one concentrated emitted fluorescence signal.

24. The device of claim 23, wherein the detector assembly further comprises two or more beam splitters for splitting the one or more emitted fluorescence signals and the at least one concentrated emitted fluorescence signal into two or more spectral bands.

25. The device of claim 24, wherein the detector assembly further comprises three beam splitters for splitting the one or more emitted fluorescence signals and the at least one concentrated emitted fluorescence signal into a first spectral band, a second spectral band and a third spectral bands respectively.

26. The device of claim 25, wherein the first spectral band ranges from about 650 nm to about 690 nm, the second spectral band ranges from about 690 nm to about 740 nm, and the third spectral band ranges from about 740 nm to about 800 nm.

27. The device of claim 24 wherein the detector assembly comprises two or more detectors, each detector configured to receive a respective portion of the one or more emitted fluorescence signals and the at least one concentrated emitted fluorescence signal from the two or more beam splitters.

28. The device of claim 27 wherein the processor module is configured for receiving data representative of each respective portion of the one or more emitted fluorescence signals and the at least one concentrated emitted fluorescence signal from the two or more detectors, and for measuring one or more fluorescence events for the individual volume of interest and normalized bulk fluorescence for the sample, based on the data.

29. The device of claim 17 further comprising a graphical user interface to display a plurality of menu options, to receive inputs from an operator and to display results for the sample.

30. The device of claim 23, wherein the controller module is coupled to the sample assembly, the light source and the detector assembly, wherein the controller module is configured to issue instructions for operation of the sample assembly, the light source and the detector assembly based on a selected menu option.

31. The device of claim 17, wherein the excitation wavelength ranges from about 300 nanometers to 1200 nanometers.

32. The device of claim 31, wherein the excitation wavelength ranges from about 600 nanometers to 800 nanometers.

33. The device of claim 32, wherein the excitation wavelength is about 640 nanometers.

34. A method for analyzing a sample comprising:
scanning a liquid sample volume with a beam spot of a single wavelength over an area of the sample volume for analysis by moving a sample carrier and the beam spot relative to each other in an R-theta scan, wherein the sample volume contains at least one fluorophore amidst bulk fluorescence of the sample defining a volume of interest, wherein the volume of interest and the beam spot have a defined relationship;
acquiring simultaneous fluorescent signal from fluorophores in the liquid sample volume, representing of one or more fluorescence events for the volume of interest where a depthwise fluorescent profile is measured using the spot and signal representing a normalized bulk fluorescence for the sample volume; and
using the simultaneous signals to distinguish fluorescent signals from fluorophores from bulk fluorescence signals in the liquid volume.

35. The method of claim 34 wherein the fluorophore is associated with an analyte in the sample.

36. The method of claim 34 wherein the fluorophore is associated with a disease condition.

37. The method of claim 36 wherein the disease condition comprises at least one of an onset, a progression, a regression, stable, an advanced condition.

* * * * *